United States Patent [19]
Oredsson

[11] Patent Number: 6,083,179
[45] Date of Patent: Jul. 4, 2000

[54] SENSOR TO DETECT CHANGES IN THE CROSS SECTION OF AN ELONGATED BODY CAVITY

[75] Inventor: Bertil Oredsson, Tyringe, Sweden

[73] Assignee: Formo Medical AB (Publ.), Tyringe, Sweden

[21] Appl. No.: 09/155,917

[22] PCT Filed: May 20, 1997

[86] PCT No.: PCT/SE97/00826

§ 371 Date: Oct. 7, 1998

§ 102(e) Date: Oct. 7, 1998

[87] PCT Pub. No.: WO97/43951

PCT Pub. Date: Nov. 27, 1997

[30] Foreign Application Priority Data

May 20, 1996 [SE] Sweden ................................. 9601897

[51] Int. Cl.$^7$ .................................................. A61B 5/103
[52] U.S. Cl. ........................... 600/587; 33/511; 604/264; 73/715
[58] Field of Search ..................... 600/482, 483, 600/485, 486, 505, 507, 560, 561, 587; 33/511, 512; 604/96, 280, 100, 264; 73/715; 128/897

[56] References Cited

U.S. PATENT DOCUMENTS

| | | |
|---|---|---|
| 3,918,164 | 11/1975 | Krautmann ............................. 33/143 C |
| 4,325,387 | 4/1982 | Helfer ..................................... 128/748 |
| 4,352,085 | 9/1982 | Herden ..................................... 338/42 |
| 4,407,301 | 10/1983 | Streisinger ............................. 600/587 |
| 4,456,013 | 6/1984 | De Rossi et al. ....................... 128/675 |
| 4,711,249 | 12/1987 | Brooks ................................... 128/748 |
| 4,873,990 | 10/1989 | Holmes et al. ......................... 600/561 |
| 5,184,619 | 2/1993 | Austin ..................................... 600/376 |
| 5,396,887 | 3/1995 | Imran ..................................... 600/587 |
| 5,452,719 | 9/1995 | Eisman et al. .......................... 600/587 |
| 5,471,756 | 12/1995 | Bolanos et al. ........................ 600/587 |
| 5,694,946 | 12/1997 | Tenerz et al. ........................... 600/587 |

*Primary Examiner*—Cary O'Connor
*Assistant Examiner*—Charles Marmor, II
*Attorney, Agent, or Firm*—Ladas & Parry

[57] ABSTRACT

A medical apparatus (1) for detecting changes in the cross section of an elongate body cavity, for example, a human urinary tract. The apparatus includes a retainer portion (60) and a sensor portion (10) connected to the retainer portion and having a sensitive body (30) of flexible material. The sensor portion has a first end portion which is fixed to the retainer device (60). The sensitive body is designed as a catheter-like device projecting from the retainer portion (60) and provided at its free end (17) with a rigid closure (37). The sensitive body is hollow and its cavity varies according to the compression of the sensitive body due to cross-sectional changes of the elongated body being examined. A pressure-sensing device indicates the pressure in the cavity and thus the cross sectional changes of the elongated body.

11 Claims, 9 Drawing Sheets

Fig.7e

SENSOR TO DETECT CHANGES IN THE CROSS SECTION OF AN ELONGATED BODY CAVITY

FIELD OF THE INVENTION

The present invention relates to a sensor to detect changes in the cross section of an elongated body cavity.

BACKGROUND AND PRIOR ART

In medical contexts, there are needs for a sensor (catheter) which is suitable for insertion in elongate and generally duct-like body cavities of varying cross-section, e.g. in the urinary tract in order to indicate changes in the cross-section of the cavity. In such duct-like cavities, the tissue pressure may, e.g. through muscular action, vary considerably between different regions of the cavity. There is, therefore, a need to be able, in addition to generally indicating changes in the cross-section of the cavity, also to be able to indicate locally occurring changes in the cross-section.

Patent specification U.S. Pat. No. 4,711,249 discloses a tubular sensor disposed to be inserted in an elongate cavity and detect changes in the dimensions of the cavity. The sensor consists of a number of sequentially disposed and spaced apart rigid tube sections in whose ends are inserted mechanically rigid bodies which sealingly connect to the surrounding tube sections. Between the ends of the tube sections, there are formed circumferentially extending grooves which are covered by elastic membranes or diaphragms. Between the membranes and the rigid bodies, spaces are formed.

Each one of the rigid bodies has a central chamber which, through an aperture, is connected to the space between the rigid body and the membrane. In its one end, the chamber has a mechanically rigid closure and in its other end a flexible closure. The space between the membrane and the rigid body as well as the chamber in the body is filled with liquid. Pressure changes in the chamber of the body are registered by a sensor abutting against the flexible closure.

The apparatus disclosed in U.S. Pat. No. 4,711,249 suffers from the drawback that only in those parts of the cylindrical sensor where the elastic membranes bridge the space which is formed between the ends of the tubular portions can the sensor register a change of the circumference of a surrounding organ. This implies that only short portions of the cylindrical sensor are capable of registering changes in the circumference of the surrounding organ. In regions which are located between the membranes, no detection of changes in the circumference of the surrounding organ takes place, in addition to which the sensor prevents the surrounding organ from assuming a circumference which is less than the circumference of the sensor.

SUMMARY OF THE INVENTION

The present invention relates to an apparatus provided with a tubular portion along which a change in the size and/or configuration of the circumference of a surrounding organ is detected regardless of where such change takes place along the cylindrical portion. This is attained by means of an apparatus comprising a catheter-like body whose internal cavity varies in response to external pressure.

BRIEF DESCRIPTION OF THE FIGURES OF THE DRAWINGS

The present invention will now be described in greater detail with reference to a number of figures, in which.

DETAILED DESCRIPTION

Figure 1:
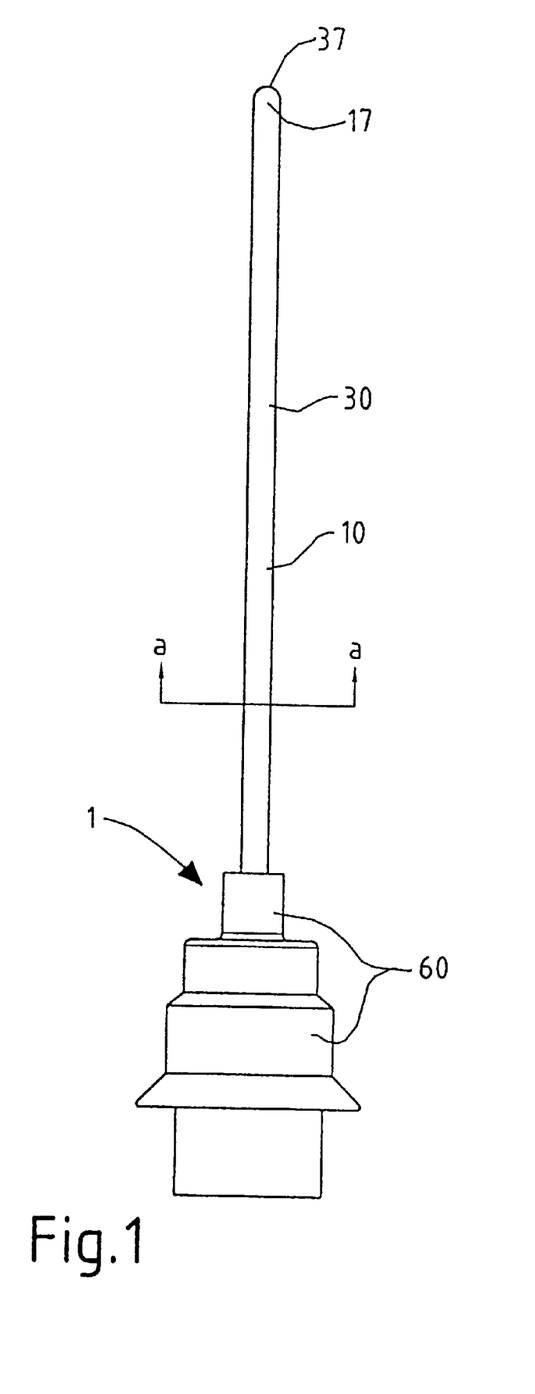
FIG. 1 is an overall view of an apparatus seen from the side.
Figure 1A:
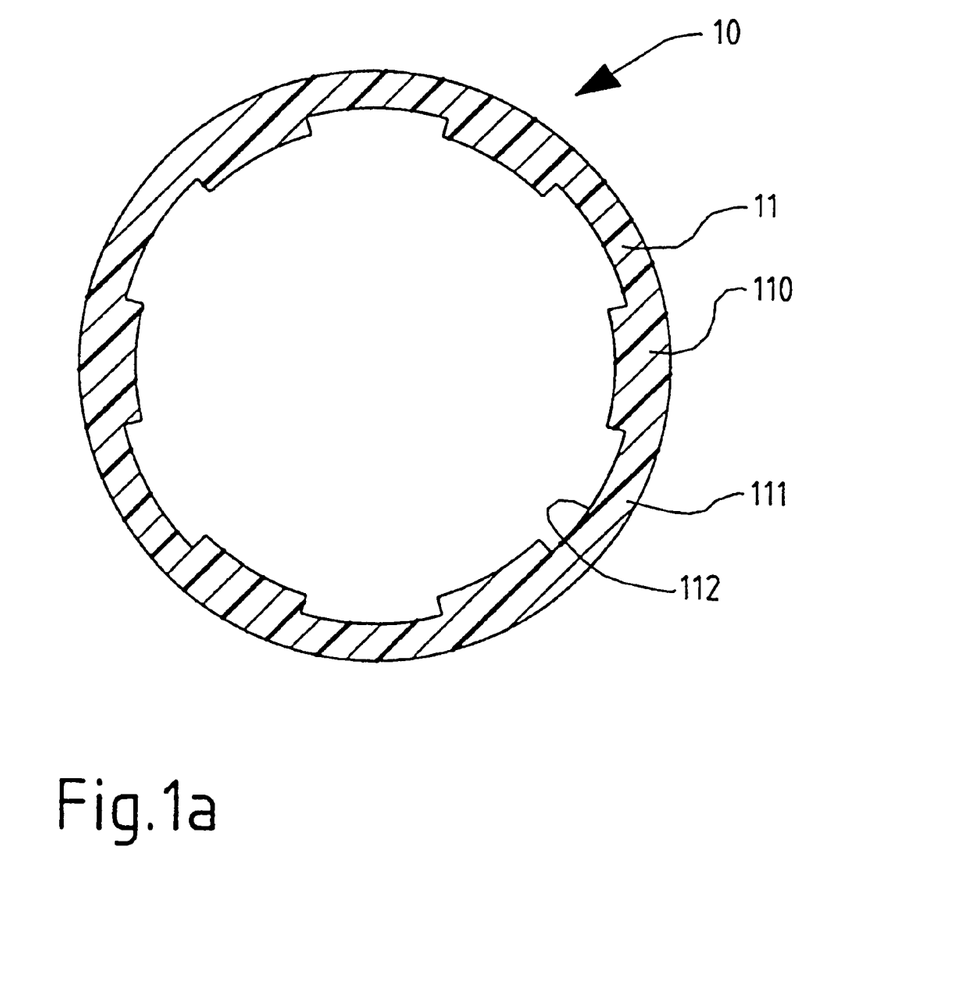
FIG. 1a is the section a—a in FIG. 1 on a magnified scale.

FIGS. 1 and 1a show an apparatus 1 which includes a substantially cylindrical portion 10 which is connected to a retainer portion 60. The cylindrical portion 10 which, hereinafter, will also be designated the sensor portion 10 of the apparatus, forms a catheter-like sensitive body 30 which projects out from the retainer portion 60 (cf. FIGS. 2–3 and 5–6). As a rule, thickened portions 110 are included in the wall 11 of the sensitive body and are disposed in the longitudinal direction of the sensitive body. In a cross-section (cf. FIG. 1a), the wall forms a sequence of material portions in the circumferential direction in which one thickened portion 110 is followed by a thinner wall portion 111 which in turn is followed by a thickened portion 110, and so on. On the inside of the wall, the thinner wall portions form a number of grooves or channels 112.

The combination of longitudinally disposed thicker material portions 110 and thinner material portions 111 involves increased rigidity against bending, at the same time as the resilience of the sensitive body 30 tranversely of the longitudinal direction of the sensitive body is retained. In certain combinations of thicknesses and widths of both the channels 112 and the thickened portions 111, increased resilience is achieved transversely of the longitudinal direction of the sensitive body at the same time as the desired flexural rigidity is maintained.

As will be apparent from the figures, the sensor portion 10 includes a first end portion 19, hereinafter generally referred to as lower end portion, which is connected to the retainer portion 60, and a second (upper) end portion 17 which is terminated by a rigid (non-resilient) closure 37. Between the lower end portion 19 and the opposing second (free) end 17 of the sensor portion, the sensor portion forms the catheter-like sensitive body which constitutes a cylindrical portion 30 of the sensor portion 10. The cavity surrounded by the cylindrical portion carries reference numeral 12. The cylindrical portion has, as a rule, a substantially circular cross-section. However, embodiments exist in which the cross-section has other configurations, e.g. is oval, is polygonal, has at least one corner, has at least one substantially straight portion, etc.

In the embodiments shown in the figures, the lower end portion 19 of the sensor portion 10 forms a conical portion 31 which is downwardly open. The lower end portion is inserted in the retainer portion 60. Below the end portion 19, there is disposed a membrane 15, 15a–c which consists of an elastically resilient material. Along its outer edge, the membrane has a circumferential anchorage ring 16. The sensor portion 10 forms, together with the membrane, a closed cavity 13. In order to form the cavity, the membrane is sealingly connected to the lower end portion 19 of the sensor portion, in that the sensor portion and the membrane are directly interconnected or in that the sensor portion 10 is sealingly connected to a first retainer device 61 which, in turn, is sealingly connected to the anchorage ring 16 of the membrane 15. A more detailed description is given below of how the lower end portion 19 and the membrane 15, 15a–c are interconnected to one another. As a rule, the cavity 13 is wholly or partly filled with a liquid and/or with a formable material, e.g. a gel. Preferably, an incompressible liquid is employed.

The retainer portion 60 includes the first (upper) retainer device 61 and a second (lower) retainer device 62. The upper portion 67 of the first retainer device forms a cavity whose inner dimensions correspond to the outer dimensions of the lower portion 19 of the sensor portion. As a rule, the upper portion of the first retainer device also surrounds a relatively short section of the sensitive body 30 of the sensor portion 10. In the region above the anchorage ring 16 of the membrane, the first retainer device 61 has a downwardly facing abutment surface 69.

In the embodiments shown in the figures, the first retainer device has a shoulder-like portion 68 whose inner wall forms the abutment surface 69. The first retainer device 61 includes, in its lower region, a substantially hollow cylindrical portion 70. In its lower end, the first retainer device is generally provided with an outwardly and downwardly directed circumferential collar 63.

The second (lower) retainer device 62 is substantially tubular in configuration. In its upper end, the end of the second retainer device forms an abutment surface 71 which abuts against the anchorage ring 16 of the membrane on that side of the anchorage ring which is opposed to the side of the anchorage ring facing towards the abutment surface 69 of the first retainer device. The second retainer device 62 is generally fixed to the first retainer device 61 by means of a snap connection 72.

Figure 2:
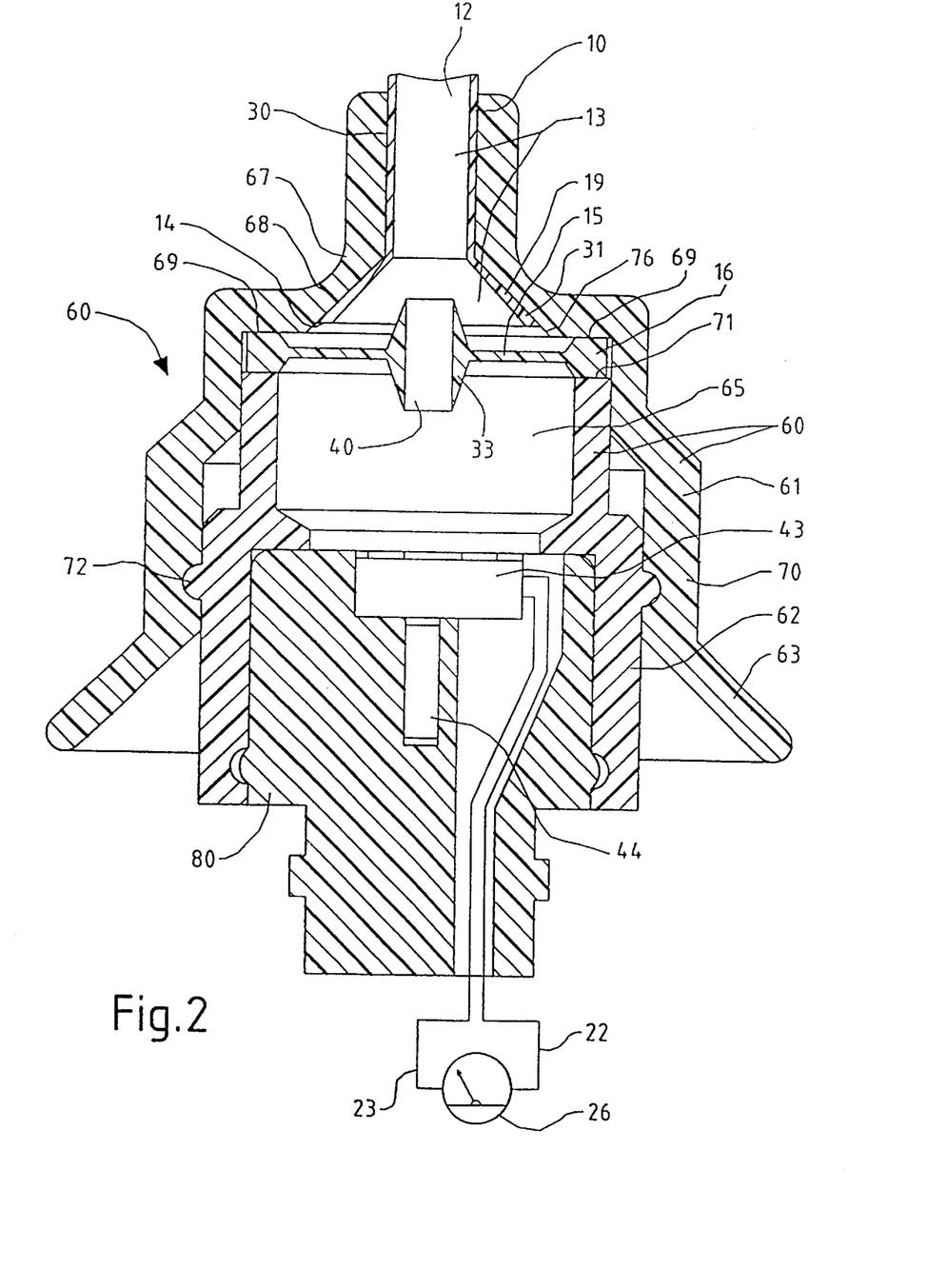
FIG. 2 is a cross-section through one embodiment of an apparatus in which this includes a Hall element for co-operation with an elastic membrane or diaphragm.
Figure 3:
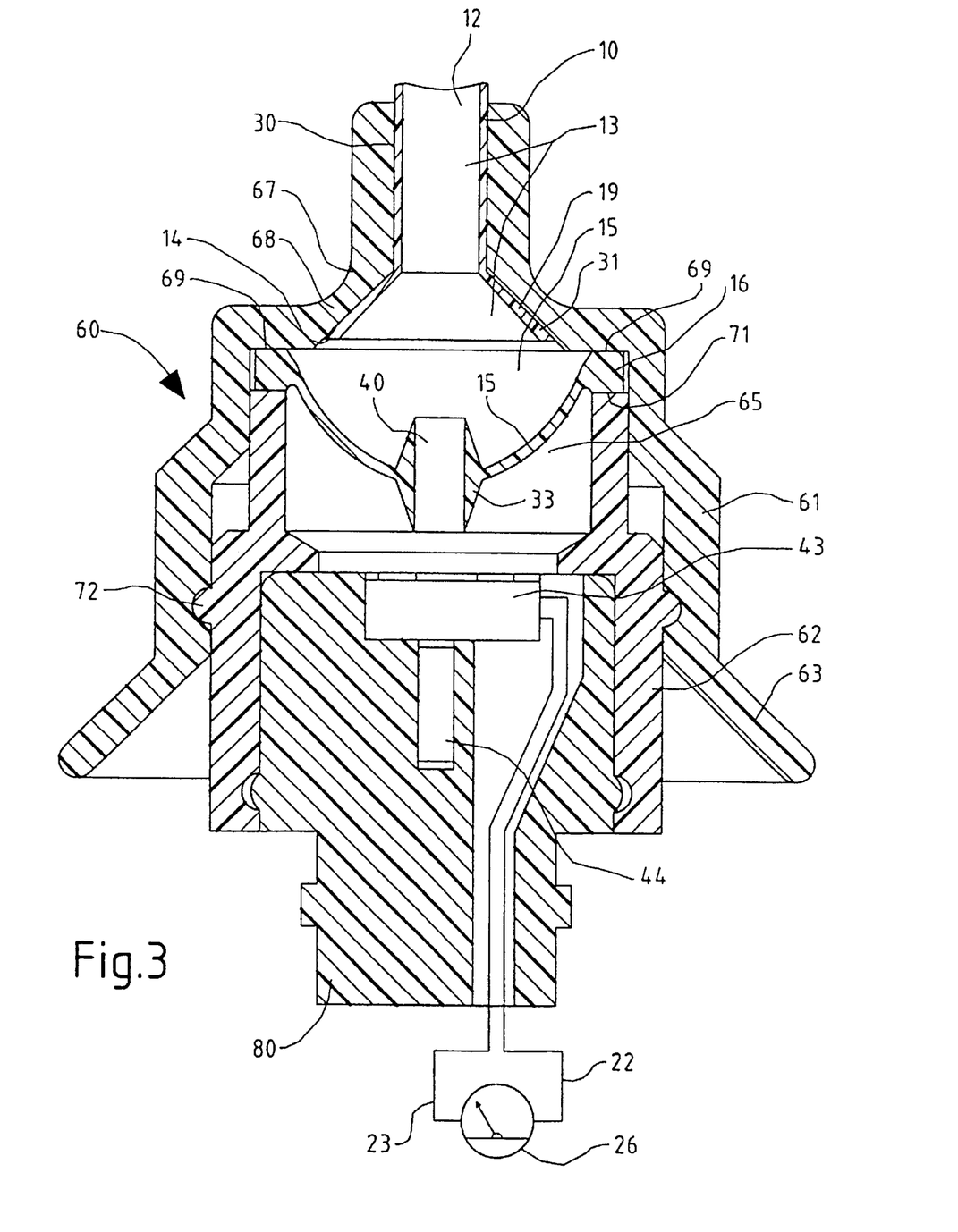
FIG. 3 is a cross-section corresponding to that of FIG. 2 where the membrane has been moved downwards in the figure.

FIGS. 2 and 3 show one embodiment of the apparatus in which the conical portion 31 of the lower end portion 19 of the sensor portion 10 has a lower edge 14 which is located a distance from the membrane 15. The conical portion is sealingly fixed to the inwardly facing surface 76 of the first retainer device 61 by means of an adhesive. In this embodiment, the first retainer device 61 forms, together with the sensor portion 10 and the membrane 15, 15a–c, the inner cavity 13, In the embodiment illustrated in FIGS. 2 and 3, the downwardly facing abutment surface 69 of the first retainer device 61 abuts against the anchorage ring 16 of the membrane. In that position in which the second retainer device 62 is fixed in relation to the first retainer device 61, the anchorage ring 16, and thereby the membrane, is fixedly retained in that the inner abutment surface 69 of the first retainer device and the abutment surface 71 of the second retainer device 62 abut under pressure against opposing sides of the anchorage ring 16. Given that the anchorage ring consists of an elastic material, a reliable seal will be obtained between the anchorage ring and the first retainer device 61.

FIGS. 2 and 3 show one embodiment of the apparatus where a first body 40 of magnetic material is secured at the membrane 15 in a central portion 33 thereof. In one preferred embodiment, the body forms a permanent magnet. As a rule, the body is of bar-like configuration so as to form a bar magnet. The central portion 33 is secured to the body 40 along its longitudinal side. Generally, the body is provided with one or more cams (not shown in the figures) to improve the fixation of the body to the membrane.

The embodiment of the apparatus 1 shown in FIGS. 2 and 3 further comprises an insert 80 in which is included a detector device 43, e.g. a Hall element for sensing magnetic field force. Above the detector device, the second holder device 62 forms a cavity 65 which allows the membrane 15 to be displaced from the starting position illustrated in FIG. 2 to the tensioned position illustrated in FIG. 3.

Figure 4A:
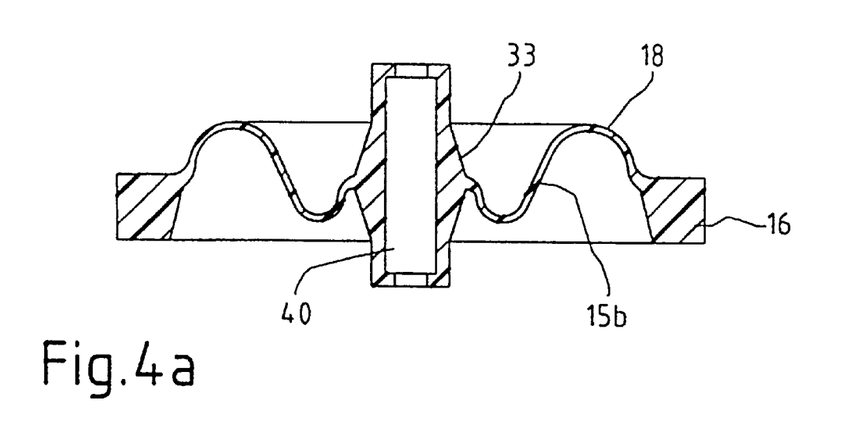
FIGS. 4a–c are cross-sections through various embodiments of the membranes.
Figure 4B:
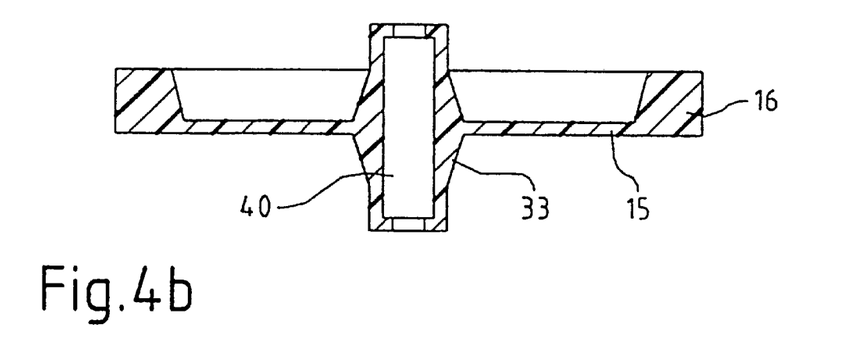

FIGS. 4a and 4b show in cross-section embodiments of the membrane 15 where the central portion 33 of the membrane projects in over the end edges of the body 40 in order to ensure fixing of the body to the membrane. The membrane 15b according to the embodiment in FIG. 4a is provided with concentrically disposed folds 18 so as to improve the sensitivity of the membrane. The figure shows one embodiment in which the cross-section is undulating as a result of the folds.

Figure 4C:
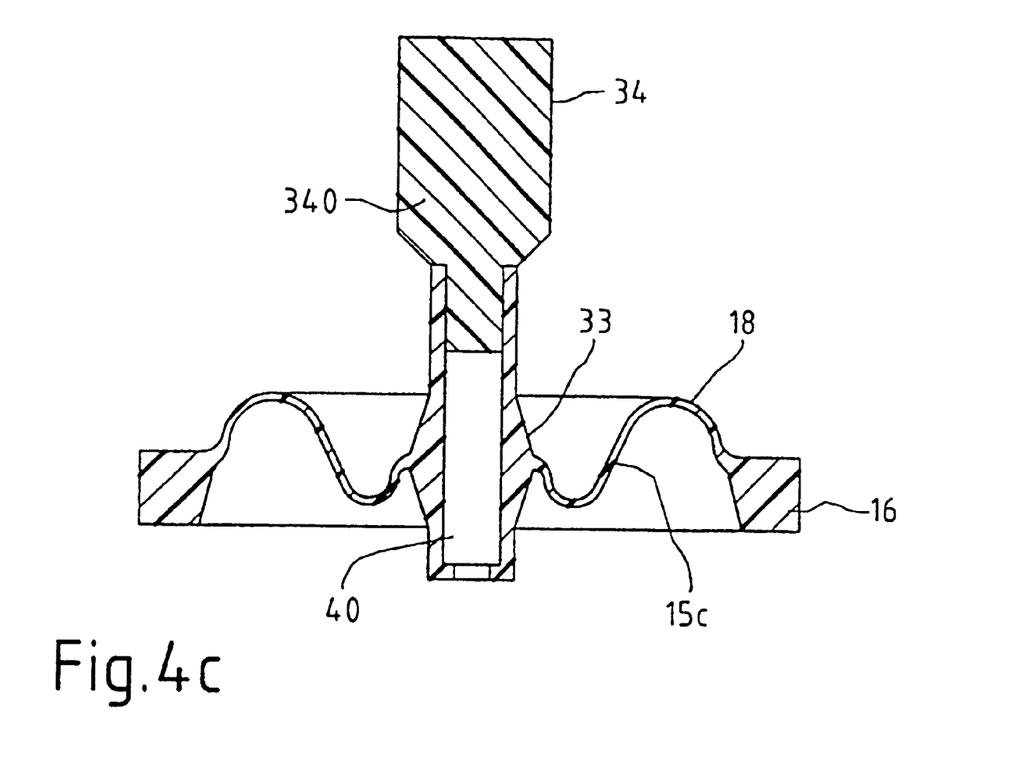

FIG. 4c shows one embodiment of the membrane 15c where a guide body 34 is connected to the central anchorage portion 33 of the membrane in a rigid interconnection. The term rigid interconnection is taken to signify that the orientation of the guide body always agrees with the orientation of the central anchorage portion 33 of the membrane 15c. The guide body 34 is secured to the membrane on that side which the membrane turns to face towards the sensitive body 30. The guide body has a cylindrical portion 340 which is dimensioned to be displaced within the sensitive body 30 with slight play to its thickened portions 110. The length of the cylindrical portion has been selected such that, on movement of the membrane, it is always located within the cavity of the sensitive body.

Figure 5:
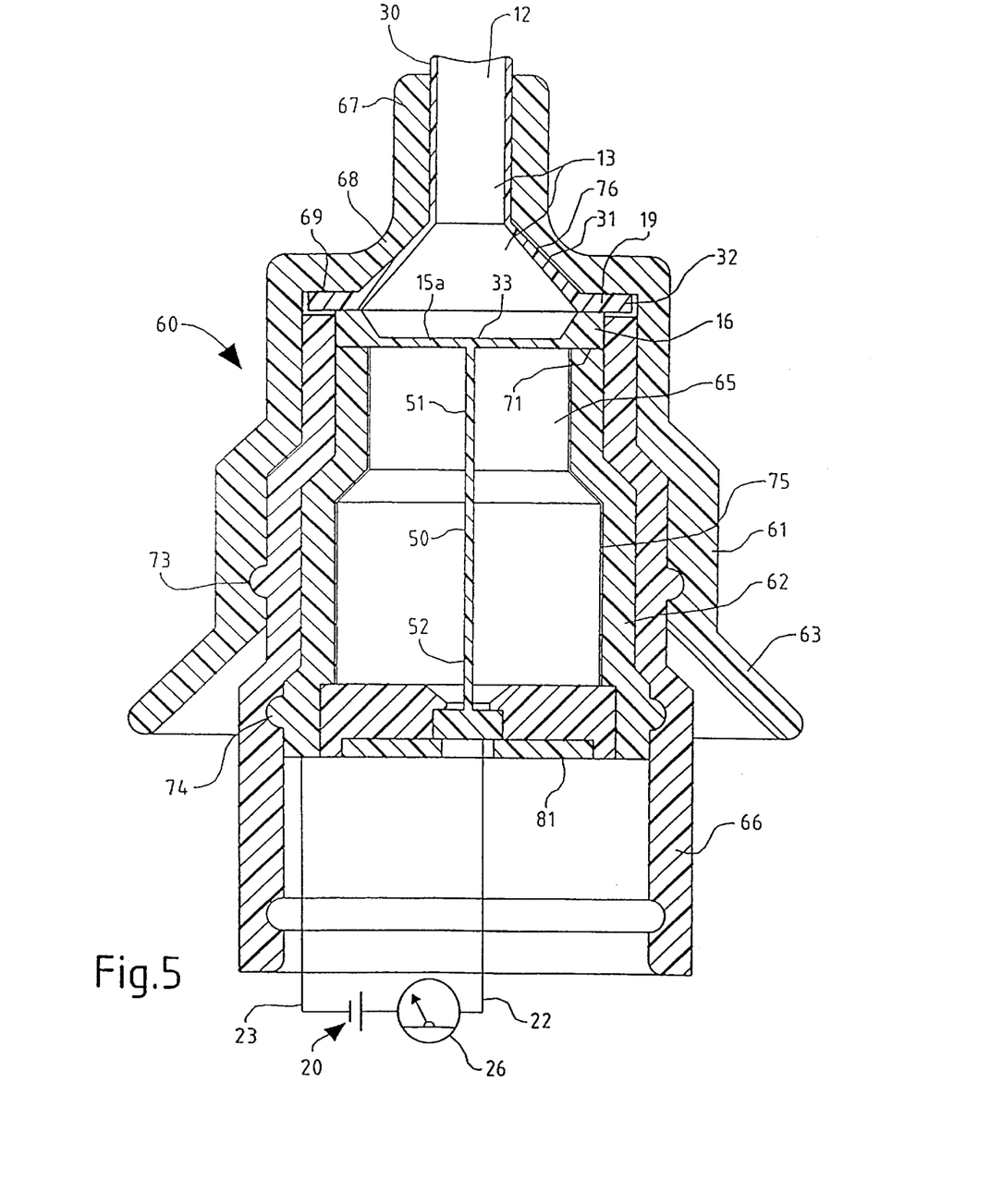
FIG. 5 is a cross-section through one embodiment of the apparatus in which this includes an electrically conductive elastic membrane.
Figure 6:
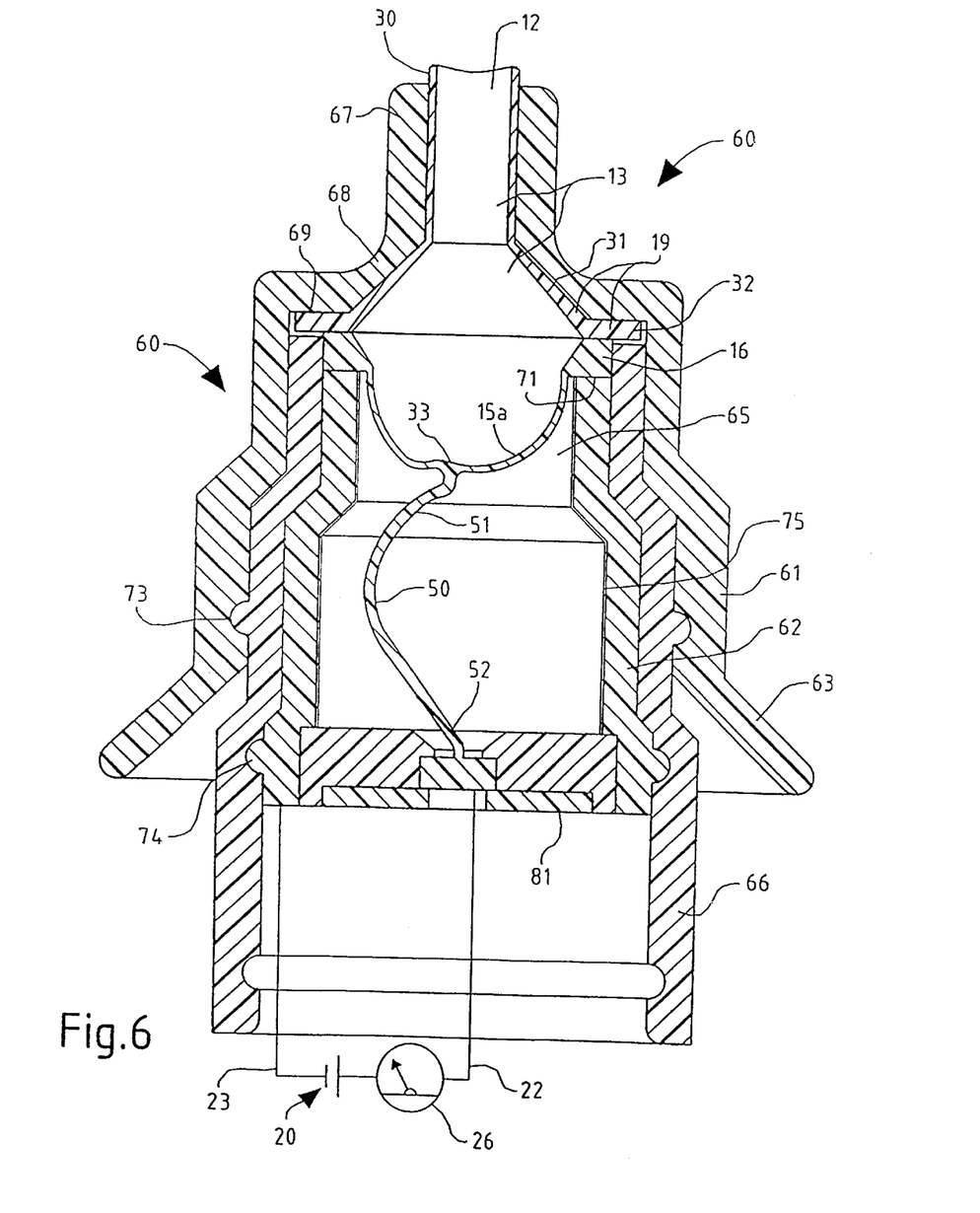
FIG. 6 is a cross-section corresponding to that of FIG. 4 in which the membrane has been moved downwards in the figure.
Figure 7A:
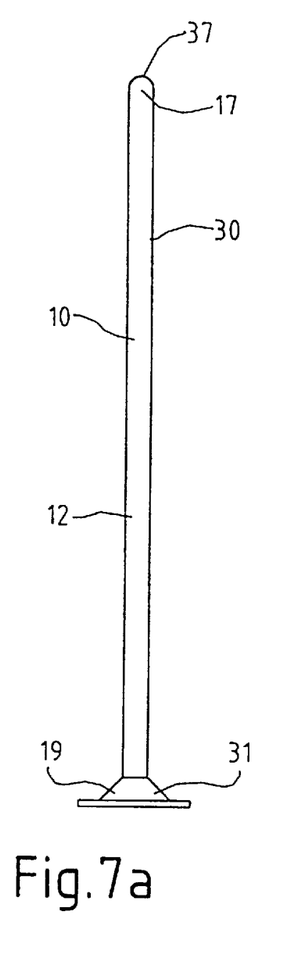
FIGS. 7a–e show embodiments of a substantially cylindrical sensor portion included in the apparatus.
Figure 7B:
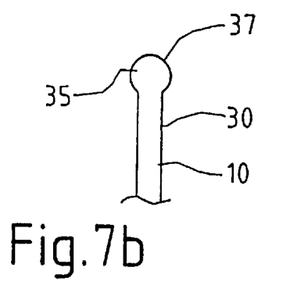
Figure 7C:
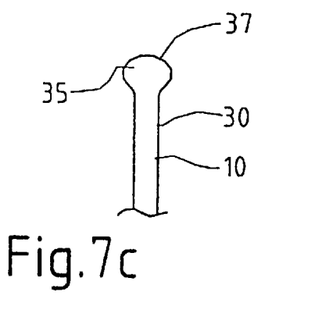
Figure 7D:
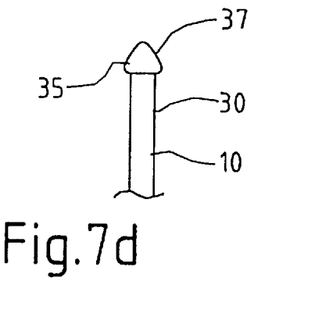
Figure 7E:
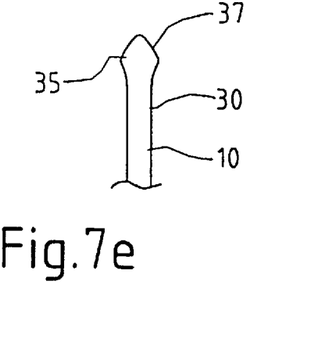

FIGS. 5 and 6 show one embodiment of the apparatus where the lower end portion 19 of the sensor portion 10 is provided with an anchorage flange 32 which downwardly terminates the lower end portion. The anchorage flange is dimensioned so as to at least partly to overlap the anchorage ring 16 of the membrane. In these embodiments, the abutment surface 69 of the first retainer device 61 abuts against the anchorage flange 32. For sealing abutment between the anchorage flange 32 and the anchorage ring 16 of the membrane, the anchorage flange and the anchorage ring are pressed against one another between the abutment surface 69 of the first retainer device 61 and the abutment surface 71 of the second retainer device 62. At the same time, the sensor portion 10 and the membrane 15 are fixed in the retainer portion 60. It will be obvious to a person skilled in the art that, in certain embodiments the anchorage flange 32 and the anchorage ring 16 are permanently and as a rule sealingly connected to one another, for example by an adhesive, a snap connecting device, etc. In these embodiments, the sensor portion 10 and the membrane 15 form a cohesive unit.

The embodiment described with connection to FIGS. 5 and 6 where the membrane is provided with the anchorage ring 16, is also employed in certain practical applications in that embodiment of the present invention which incorporates the body 40 of magnetic material.

FIGS. 5 and 6 show an embodiment of the retainer portion 60 in which an intermediate portion 66 is disposed between the first retainer device 61 and the second retainer device 62. The intermediate portion is fixed to the first retainer device by a snap connection 73, and to the second retainer device by a snap connection 74.

In certain embodiments, the detector device 43 is disposed between the first body 40 and the second body 44 which also consists of magnetic material. In one preferred embodiment, the second body 44 forms a permanent magnet. The bodies are, as a rule, of bar-like design so as to form bar magnets. In those embodiments where both the first and the second body are designed as bar magnets, these are generally oriented such that the southern pole of the one magnet is turned to face towards the northern pole of the other magnet.

For the first body 40 and the second body 44, a substantially circular cross-section is generally selected, but other cross-sections of these bodies occur. However, at least for the first body 40, the substantially circular cross-section is generally selected. In certain embodiments, the axial length of the bodies is so slight that the bodies assume plate-like shape.

By the intermediary of electric conductors 22, 23, a measurement instrument 26 is connected to the detector device 43 for registering the signal which this emits as a measurement of the magnitude of the force of the detected magnetic field.

FIGS. 5 and 6 also show one embodiment of the present invention in which the membrane 15a is, in its central portion 33, connected to a downwardly directed rod 50. The upper portion 51 of the rod is connected to the central portion 33 of the membrane 15a, and the lower portion 52 of the rod is fixed to a support member 81 provided in the second retainer device 62. The rod is generally of slight thickness and is made from a flexible and electrically conducted material. It is dimensioned to form an arc on axial loading. The membrane consists of an elastically resilient and electrically conductive material. The conductive capacity of the material in the membrane varies in response to the bending to which the material is subjected. One example of such a material is electrically conductive silicon rubber. The membrane and the rod often form an integral unit. The inner surface of the second retainer device 62 is coated with a layer 75 of electrically insulating material. The electric conductors 22, 23 are connected to the lower portion 52 of the rod and to the second retainer device 62 which also consists of an electrically conductive material. The rod and the second retainer device are included in an electric circuit which further includes a voltage source 20 and the registration and/or indicator device 26.

The cavity 65 formed by the second retainer device 62 above the detector device allows the membrane 15a to be displaced from the starting position illustrated in FIG. 5 to the tensioned position illustrated in FIG. 6. On displacement of the membrane towards the support device 81, the central portions of the rod are moved aside in an area between the upper and lower portions of the rod, as is apparent from FIG. 6. The rod is dimensioned such that the lower portion 52 of the rod 50 is fixed to the support device 81 a distance from the central portion 33 of the membrane which is sufficiently large for the rod normally not to come into contact with the second surface of the second retainer device 62 when the membrane 15a assumes its maximum tensioned position (cf. FIG. 6).

In the embodiment described in FIGS. 2–3, the detector device 43 is disposed a distance from the body 40 which is sufficiently great for the body, on normal use of the apparatus, not to come into contact with the detector device when the membrane 15 assumes its maximum tensioned position (cf. FIG. 3). This effect is achieved in that the size of the closed cavity 13 in the unaffected state (no outer pressure applied against the sensitive body 30) and the distance between the central anchorage portion 33 of the membrane and the detector device 43 have been selected such that on maximum calculated compression of the portion 30, the central anchorage portion 33 or the body 40 fixed thereto is never displaced to positions in which the anchorage portion 33 or the body 40 is in contact with the support device 81 or with the detector device 43.

As has already been intimated, in the embodiment according to FIGS. 5–6, the length of the rod 50 has been selected such that on calculated maximum compressure of the portion 30 of the sensor portion, no part of the rod is located in contact with the inner defining surface of the second retainer device 62. The insulation layer 75 is provided so as to avoid measurement error in the event of unforeseen contact between the inner defining surface of the second retainer device and the rod 50.

FIGS. 7a–e show embodiments of the sensitive body 30 of the sensor. In the embodiments illustrated in FIGS. 7b–e, the sensitive body is, in its free end portion 17, provided with a flared portion 35. This flared portion contributes to keeping the sensitive body in position in the vessel or the body for which the intention is to register changes in size and/or shape.

The figures show one embodiment where the first (upper) retainer device 61 constitutes an outer retainer device which partly surrounds the second (lower) retainer device. It will be obvious that, in other embodiments, the second (lower) retainer device constitutes an outer retainer device which at least partly surrounds the first retainer device. In this embodiment, the second retainer device is, as a rule, provided with the outwardly directed collar 63.

It will be obvious to a person skilled in the art that, on application of the described technique, the disclosed joining of parts or devices included in the apparatus by means of snap catch devices may, when necessary, be replaced by a technique which is adapted to meet the demands placed by the practical application under consideration. Examples of such techniques are screw connections, hot welding, glue joints, etc.

When the apparatus according to the invention is reduced into practice, the substantially cylindrical portion 30 (the sensitive body 30) of the sensor portion 10 is inserted into the cavity which is to be examined, for example a patient's urinary tract. When the circumference of any part of the cavity is reduced, a corresponding part of the sensitive body 30 is compressed, the size of the cavity 12 of the sensitive body being reduced. The reduction of the size of the cavity results in the pressure in the cavity increasing, which entails that the central portion 33 of the membrane 15, 15a–c is displaced towards the detector device 43 or towards the support device 81. When the circumference of the space increases in the region of the compressed portion of the sensitive body, the pressure against the sensitive body is reduced, the resilient return properties of the membrane entailing that the central portion 33 of the membrane is displaced away from the support device. The size of the displacement is determined by the size of the pressure reduction. A change of the outer pressure against the sensitive body 30 will thus entail a corresponding change in the stretching of the membrane.

As a rule, the sensitive body has been dimensioned to be compressed by forces which are substantially less than the forces which are required to displace the central portion of the membrane from its rest position. As a result, the membrane is wholly determinative of the sensitivity of the apparatus.

In the embodiment illustrated in FIGS. 2–3, displacement of the membrane 15 entails that the magnetic field force registered by the detector device 43 is changed, a change which entails that the registration and/or indicator device 26 connected to the detector device registers and/or indicates the change of the magnetic field force. This indication takes place for example in that the size of and/or the change of measured current or voltage is registered on a magnetic tape, is shown by a change in indication of a measurement instrument, by changed light indication (such as lighting or extinguishing of, for example, one or more lamps or one or more LEDs), etc.

In the embodiment illustrated in FIG. 4c, the guide body 34 is displaced within the cavity 12 of the sensitive body 30 with slight play between the guide body and the thickened portions 110. This displacement takes place at the same rate as the movement of the central portion 33 of the membrane. The guide body rigidifies the central portion of the membrane. This thereby avoids undesired deformation of the membrane, which could lead to erroneous indications of the size of the compression of the sensitive body 30. The channels 112 located between the thickened portions ensure the redistribution of pressure medium which occurs on compression or expansion of the sensitive body 30 and which is indicated by the tensioned position of the membrane.

On downward displacement of the membrane, the embodiment of the rod 50 shown in FIGS. 5–6 is moved aside in a region between the upper and lower portions 51 and 52, respectively, of the rod. The second retainer device 62, the membrane 15a and the rod 50 are included in the electric circuit which moreover encompasses the two conductors 22, 23, the voltage source 20 and the registration and/or indication device 26. When the membrane 15a is stretched, the resistance in the electric circuit is changed, which is registered and/or indicated by the registration and/or indication device 26.

It will be obvious to a person skilled in the art that, also in the planar embodiment of the membrane illustrated in FIGS. 5–6, the change of the position of the membrane is registered and/or indicated by a device 26 of a design corresponding to that previously described in connection with FIGS. 2–3.

The apparatus according to the present invention is generally applicable for medical purposes. Registration or indication of contractions in a urinary tract may be of extremely great value, for example in connection with the treatment of incontinence.

In the foregoing description, use has been made of the expressions "upper", "lower", "downward", "below" and other corresponding expressions. These determinations have merely been employed to simplify the description and are only related to the orientation the apparatus has in the figures. It will be obvious to a person skilled in the art that the apparatus, as well as part for devices included therein, may have any optional spatial orientation.

The above detailed description has referred to but a limited number of embodiments of the present invention, but a person skilled in the art will readily perceive that the present invention encompasses a large number of embodiments without departing from the scope of the appended Claims.

What is claimed is:

1. A medical apparatus for detecting changes in cross-section of an elongate body cavity, said apparatus comprising a retainer portion and a sensor portion connected to the retainer portion and including a sensitive body of flexible material, said sensitive body having a substantially hollow, cylindrical shape, the sensor portion having a first end portion and a second end portion, the first end portion of the sensor portion being connected to the retainer portion, said sensitive body having a closed cavity at least partly filled with a deformable medium, and a pressure sensing device for sensing pressure in the closed cavity, said sensor portion being mechanically fixed to the retainer portion only at said first end portion; said sensitive body being in the form of a catheter projecting from the retainer portion into the body cavity and including a closure at a free end thereat, such that cross-sectional changes in said body cavity produce pressure changes of said pressure sensing device, said sensor portion including a guide body fixed at said first end portion and communicating with said closed cavity to be subject to the pressure therein, said pressure sensing device comprising a flexible membrane supporting said guide body from said retainer portion to undergo movement in response to pressure changes in said closed body, and means for sensing the movement of said membrane.

2. The apparatus as claimed in claim 1, wherein said sensitive body has a number of thickened portions extending longitudinally of the sensitive body and arranged in circumferential spaced relation therein.

3. The apparatus as claimed in claim 2, wherein said thickened portions extend inwardly from a wall of the sensitive body.

4. The apparatus as claimed in claim 2, wherein said guide body is secured to a central portion of said membrane; and is disposed to be displaceable in relation to the thickened portions of the sensitive body portion.

5. The apparatus as claimed in claim 4, wherein said means for sensing movement of said membrane comprises a magnet secured to said membrane; and a fixed detector device cooperating with said magnet to detect movement thereof.

6. The apparatus as claimed in claim 5, wherein said magnet is secured to the central portion of the membrane.

7. The apparatus as claimed in claim 5, comprising a second magnet on said membrane spaced from the first said magnet; said detector device being disposed between the first and second magnets.

8. The apparatus as claimed in claim 7, wherein said magnets are bar magnets.

9. The apparatus as claimed in claim 8, wherein said bar magnets are oriented such that the south pole of one magnet faces the north pole of the other magnet.

10. The apparatus as claimed in claim 4, wherein said membrane consists of an elastically resilient and electrically conductive material whose electric conductive capacity varies with stretching of the material; said membrane being included in an electrical circuit including said means for sensing the movement of the membrane which senses change of resistance in the circuit based on a change in configuration of the membrane.

11. The apparatus as claimed in claim 10, comprising a contact pin of elastic and electrically conductive material in said circuit; said contact pin being disposed between a central portion of the membrane and a support device provided in the retainer portion.

* * * * *